US009284269B2

(12) United States Patent
Jones et al.

(10) Patent No.: US 9,284,269 B2
(45) Date of Patent: Mar. 15, 2016

(54) POLYMORPHS OF N-(2-METHOXYBENZOYL)-4-[(METHYLAMINOCARBONYL)AMINO] BENZENESULFONAMIDE

(71) Applicant: Syngenta Limited, Guildford Surrey (GB)

(72) Inventors: Ian Kevin Jones, Bracknell Berkshire (GB); Neil George, Bracknell Berkshire (GB); John Hone, Bracknell Berkshire (GB)

(73) Assignee: Syngenta Limted, Guildford, Surrey (GB)

( * ) Notice: Subject to any disclaimer, the term of this patent is extended or adjusted under 35 U.S.C. 154(b) by 0 days.

(21) Appl. No.: 14/376,462

(22) PCT Filed: Feb. 8, 2013

(86) PCT No.: PCT/EP2013/052534
§ 371 (c)(1),
(2) Date: Aug. 4, 2014

(87) PCT Pub. No.: WO2013/117691
PCT Pub. Date: Aug. 15, 2013

(65) Prior Publication Data
US 2015/0005166 A1    Jan. 1, 2015

(30) Foreign Application Priority Data
Feb. 9, 2012    (GB) .................................. 1202393.3

(51) Int. Cl.
*C07C 311/51*    (2006.01)
*A01N 25/32*    (2006.01)
*A01N 47/30*    (2006.01)

(52) U.S. Cl.
CPC .............. *C07C 311/51* (2013.01); *A01N 25/32* (2013.01); *A01N 47/30* (2013.01); *C07B 2200/13* (2013.01)

(58) Field of Classification Search
None
See application file for complete search history.

(56) References Cited

U.S. PATENT DOCUMENTS
5,215,570 A    6/1993    Burckhardt et al.

OTHER PUBLICATIONS
International Search Report dated Apr. 22, 2013 for International Patent Application No. PCT/EP2013/052534.

*Primary Examiner* — Mina Haghighatian
*Assistant Examiner* — Erin Hirt
(74) *Attorney, Agent, or Firm* — R. Kody Jones

(57) ABSTRACT
The present invention relates to solid forms of herbicide safeners, to processes for their preparation, compositions comprising the solid forms and methods of their use as safeners.

7 Claims, 5 Drawing Sheets

POLYMORPHS OF N-(2-METHOXYBENZOYL)-4-[(METHYL-AMINOCARBONYL)AMINO]BENZENESULFONAMIDE

RELATED APPLICATION INFORMATION

This application is a 371 of International Application No. PCT/EP2013/052534, filed Feb. 8, 2013, which claims priority to GB Patent Application No. 1202393.3, filed Feb. 9, 2012, the contents of which are incorporated herein by reference herein.

This invention relates to solid forms of N-acylsulfamoylphenylurea safeners, to processes for their preparation, compositions comprising the solid forms and methods of their use as safeners.

Herbicide safeners selectively protect crop plants from herbicide damage without reducing activity in target weed species. They are used commercially to improve herbicide selectivity between crop and weed species and can be applied, for example, as a mixture with the herbicide or as a seed-treatment to the crop seed prior to sowing. U.S. Pat. No. 5,215,570 discloses that certain N-acylsulfamoylphenylurea derivatives can act as safeners. In particular the compound of formula (I), N-(2-methoxybenzoyl)-4-[(methylaminocarbonyl)amino]benzenesulfonamide, is disclosed:

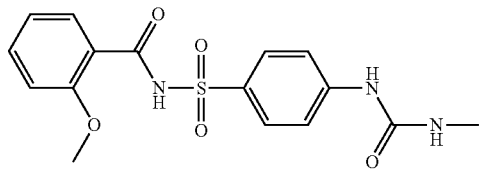

(I)

This safener is suitable for protecting cultivated plants from the phytotoxic action of, for example, acylcyclohexanedione herbicides, sulphonylurea herbicides, chloroacetanilide herbicides and aryloxyphenoxypropionic acid herbicides.

New solid forms of this compound, their compositions and methods of their preparation and use have now been discovered.

Accordingly, the present invention relates to novel crystalline forms of the safener of formula (I).

In one aspect of the invention, there is provided a crystalline polymorph of the compound of formula I, designated Form 1, which is characterised by a powder X-ray diffraction pattern expressed in terms of 2θ angles, wherein the powder X-ray diffraction pattern comprises at least three, at least four, at least five, at least six, at least 7 or all 2θ angle values (in degrees) selected from the group comprising 7.4±0.2, 9.3±0.2, 11.7±0.2, 12.0±0.2, 14.3±0.2, 15.1±0.2, 17.4±0.2 and 19.0±0.2. These 2θ angle values are derived from a powder X-ray diffraction pattern of polymorph Form 1 obtained using the method of Example 1a. The values were generated using a wavelength of 1.54056 Å with a 2θ step size of 0.02°.

In another aspect, the crystalline polymorph of the compound of formula I designated Form 1 has a melting point of 198° C.±5° C. This melting point is obtained using Differential Scanning Calorimetry (DSC) with a heating rate of 10° C./minute.

In a further aspect of the invention, there is provided a crystalline polymorph of the compound of formula I, designated Form 2, which is characterised by the unit cell parameters of its single crystal as shown in Table 1. The polymorph was obtained using the method of Example 1d.

TABLE 1

| Class | Orthorhombic |
|---|---|
| Space Group | Pbca |
| Cell Lengths (Å) | a = 19.38(5) |
|  | b = 7.34(5) |
|  | c = 22.95(5) |
| Cell Angles (°) | α = 90.00 |
|  | β = 90.00 |
|  | γ = 90.00 |
| Volume (Å$^3$) | 3264.8(5) |
| Z | 8 |

In the table,
a, b, c = Length of the edges of the unit cell;
α, β, γ = Angles of the unit cell; and
Z = molecules per cell.

Thus, in one aspect of the present invention, the crystalline polymorph of the invention designated Form 2 has the following lattice parameters: a=19.38(5), b=7.34(5), c=22.95(5), α=90.00, β=90.00, γ=90.00 and volume=3264.8(5) Å$^3$.

In another aspect of the invention, the crystalline polymorph of the invention designated Form 2 is characterised by a powder X-ray diffraction pattern expressed in terms of 2θ angles, wherein the powder X-ray diffraction pattern comprises
  (a) at least one 2θ angle value at 9.0±0.2; and
  (b) one 2θ angle value at 21.7±0.2; and
  (c) at least three, at least four, at least five, at least six or all 2θ angle values selected from the group comprising 7.7±0.2, 11.9±0.2, 13.4±0.2, 15.0±0.2, 15.6±0.2, 16.1±0.2 and 18.0±0.2.

In one embodiment, the crystalline polymorph of the invention designated Form 2 is characterised by a powder X-ray diffraction pattern expressed in terms of 2θ angles, wherein the powder X-ray diffraction pattern comprises
  (a) at least one 2θ angle value at 9.0±0.2; and
  (b) one 2θ angle value at 21.7±0.2; and
  (c) at least three 2θ angle values selected from the group comprising 7.7±0.2, 11.9±0.2, 13.4±0.2, 15.0±0.2, 15.6±0.2, 16.1±0.2 and 18.0±0.2.

In another embodiment, the crystalline polymorph of the invention designated Form 2 is characterised by a powder X-ray diffraction pattern expressed in terms of 2θ angles, wherein the powder X-ray diffraction pattern comprises
  (a) at least one 2θ angle value at 9.0±0.2; and
  (b) one 2θ angle value at 21.7±0.2; and
  (c) at least four 2θ angle values selected from the group comprising 7.7±0.2, 11.9±0.2, 13.4±0.2, 15.0±0.2, 15.6±0.2, 16.1±0.2 and 18.0±0.2.

In another embodiment, the crystalline polymorph of the invention designated Form 2 is characterised by a powder X-ray diffraction pattern expressed in terms of 2θ angles, wherein the powder X-ray diffraction pattern comprises
  (a) at least one 2θ angle value at 9.0±0.2; and
  (b) one 2θ angle value at 21.7±0.2; and
  (c) at least five 2θ angle values selected from the group comprising 7.7±0.2, 11.9±0.2, 13.4±0.2, 15.0±0.2, 15.6±0.2, 16.1±0.2 and 18.0±0.2.

In another embodiment, the crystalline polymorph of the invention designated Form 2 is characterised by a powder X-ray diffraction pattern expressed in terms of 2θ angles, wherein the powder X-ray diffraction pattern comprises
  (a) at least one 2θ angle value at 9.0±0.2; and
  (b) one 2θ angle value at 21.7±0.2; and
  (c) at least six 2θ angle values selected from the group comprising 7.7±0.2, 11.9±0.2, 13.4±0.2, 15.0±0.2, 15.6±0.2, 16.1±0.2 and 18.0±0.2.

In another embodiment, the crystalline polymorph of the invention designated Form 2 is characterised by a powder X-ray diffraction pattern expressed in terms of 2θ angles, wherein the powder X-ray diffraction pattern comprises
- (a) at least one 2θ angle value at 9.0±0.2; and
- (b) one 2θ angle value at 21.7±0.2; and
- (c) all 2θ angle values selected from the group comprising 7.7±0.2, 11.9±0.2, 13.4±0.2, 15.0±0.2, 15.6±0.2, 16.1±0.2 and 18.0±0.2.

These 2θ angle values are derived from a powder X-ray diffraction pattern of polymorph Form 2 obtained using the method of Example 1d. The values are generated using a wavelength of 1.54056 Å with a 2θ step size of 0.02°.

In a further aspect, the crystalline polymorph of the invention designated Form 2 has a melting point of 216° C.±5° C. This melting point is obtained using Differential Scanning Calorimetry (DSC) with a heating rate of 10° C./minute.

In a yet further aspect of the invention, there is provided a crystalline polymorph of—the compound of formula I, designated Form 3, which is characterised by the unit cell parameters of its single crystal as shown in Table 2. The polymorph was obtained using the method of Example 1e.

TABLE 2

| Class | Monoclinic |
|---|---|
| Space Group | P2$_1$/n |
| Cell Lengths (Å) | a = 7.96(5) |
| | b = 23.56(5) |
| | c = 9.11(5) |
| Cell Angles (°) | α = 90.00 |
| | β = 92.58(5) |
| | γ = 90.00 |
| Volume (Å$^3$) | 1708.2(5) |
| Z | 4 |

In the table,
a, b, c = Length of the edges of the unit cell;
α, β, γ = Angles of the unit cell; and
Z = molecules per cell.

Thus, in one aspect of the present invention, the crystalline polymorph of the invention designated Form 3 has the following lattice parameters: a=7.96(5), b=23.56(5), c=9.11(5), α=90.00, β=92.58(5), γ=90.00 and volume=1708.2(5) Å$^3$.

In another aspect of the invention, the crystalline polymorph of the invention designated Form 3 is characterised by a powder X-ray diffraction pattern expressed in terms of 2θ angles, wherein the powder X-ray diffraction pattern comprises
- (a) one 2θ angle value at 16.9±0.2; and
- (b) one 2θ angle value at 18.9±0.2; and
- (c) at least three, at least four, at least five, at least six, at least seven, at least eight, at least nine, at least ten or all 2θ angle values selected from the group comprising 7.5±0.2, 12.3±0.2, 13.4±0.2, 14.4±0.2, 14.9±0.2, 15.8±0.2, 18.3±0.2, 20.9±0.2, 21.9±0.2, 22.6±0.2 and 23.8±0.2.

In one embodiment, the crystalline polymorph of the invention designated Form 3 is characterised by a powder X-ray diffraction pattern expressed in terms of 2θ angles, wherein the powder X-ray diffraction pattern comprises
- (a) one 2θ angle value at 16.9±0.2; and
- (b) one 2θ angle value at 18.9±0.2; and
- (c) at least three 2θ angle values selected from the group comprising 7.5±0.2, 12.3±0.2, 13.4±0.2, 14.4±0.2, 14.9±0.2, 15.8±0.2, 18.3±0.2, 20.9±0.2, 21.9±0.2, 22.6±0.2 and 23.8±0.2.

In another embodiment, the crystalline polymorph of the invention designated Form 3 is characterised by a powder X-ray diffraction pattern expressed in terms of 2θ angles, wherein the powder X-ray diffraction pattern comprises
- (a) one 2θ angle value at 16.9±0.2; and
- (b) one 2θ angle value at 18.9±0.2; and
- (c) at least six 2θ angle values selected from the group comprising 7.5±0.2, 12.3±0.2, 13.4±0.2, 14.4±0.2, 14.9±0.2, 15.8±0.2, 18.3±0.2, 20.9±0.2, 21.9±0.2, 22.6±0.2 and 23.8±0.2.

In another embodiment, the crystalline polymorph of the invention designated Form 3 is characterised by a powder X-ray diffraction pattern expressed in terms of 2θ angles, wherein the powder X-ray diffraction pattern comprises
- (a) one 2θ angle value at 16.9±0.2; and
- (b) one 2θ angle value at 18.9±0.2; and
- (c) at least nine 2θ angle values selected from the group comprising 7.5±0.2, 12.3±0.2, 13.4±0.2, 14.4±0.2, 14.9±0.2, 15.8±0.2, 18.3±0.2, 20.9±0.2, 21.9±0.2, 22.6±0.2 and 23.8±0.2.

In another embodiment, the crystalline polymorph of the invention designated Form 3 is characterised by a powder X-ray diffraction pattern expressed in terms of 2θ angles, wherein the powder X-ray diffraction pattern comprises
- (a) one 2θ angle value at 16.9±0.2; and
- (b) one 2θ angle value at 18.9±0.2; and
- (c) all 2θ angle values selected from the group comprising 7.5±0.2, 12.3±0.2, 13.4±0.2, 14.4±0.2, 14.9±0.2, 15.8±0.2, 18.3±0.2, 20.9±0.2, 21.9±0.2, 22.6±0.2 and 23.8±0.2.

These 2θ angle values are derived from a powder X-ray diffraction pattern of polymorph Form 3 obtained using the method of Example 1e. The values are generated using a wavelength of 1.54056 Å with a 2θ step size of 0.02°.

In another aspect, the crystalline polymorph of the invention designated Form 3 has a melting point of 202° C.±5° C. This melting point is obtained using Differential Scanning Calorimetry (DSC) with a heating rate of 10° C./minute.

In the context of the present invention, a polymorph is a particular crystal form of a chemical compound that can exist in more than one crystal form in the solid state. A crystal form of a compound contains the constituent molecules arranged in orderly repeating patterns extending in all three spatial dimensions (in contrast, an amorphous solid form has no long-range order in the position of molecules). Different polymorphs of a compound have different arrangements of atoms and or molecules in their crystal structure. When the compound is a biologically active compound, such as a safener, the difference in crystal structures can lead to different polymorphs having differing chemical, physical and biological properties. Properties which may be affected include crystal shape, density, hardness, colour, chemical stability, melting point, hydroscopicity, suspensibility, dissolution rate and biological availability. As such, a specific polymorph may have properties which make it more advantageous in a particular use relative to another polymorph of the same compound: in particular, the physical, chemical and biological properties listed above can have a significant effect on the development of production methods and formulations and the quality and efficacy of plant treatment agents, such as safeners. It is noted that predicting whether the solid state of a compound may be present as more than one polymorph is not possible and nor is it possible to predict the properties of any of these crystal forms. In particular, in the context of the present invention, it has been found that the compound of formula (I) can exist as a stable polymorph designated Form 2 which is advantageous due to its stability in comparison with Form 1 and Form 3 which decreases the amount of crystallization occurring in formulations of the compound of formula (I) as the metastable forms become, over time, the stable form. Such crystallization is detrimental because it can lead to thickening and potentially solidification of the formulation and/or large crystals, which can lead to blockages in application equipment e.g. in spray nozzles in agricultural application machinery. As such, the polymorph designated Form 2 is preferred.

The present invention also relates to methods for the preparation of the polymorphs of the invention either directly (i.e. not starting with other solid forms of the compound of formula I) or by conversion of other solid forms of the compound of formula I.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC. Single crystal X-ray diffraction is especially useful in identifying crystal structures.

The polymorphs of the invention may be applied in unchanged form but are more preferably incorporated into agrochemical compositions by conventional means. Accordingly, in a further aspect, the invention provides an agrochemical composition comprising a polymorph of the invention as defined above and at least one an agriculturally acceptable carrier or diluent. In one embodiment, the composition of the invention further comprises at least one herbicide. Preferably, the mixing ratio of the at least one herbicide to safener is from 100:1 to 1:100, especially from 20:1 to 1:20.

In a further aspect, the present invention provides a method for protecting crops of useful plants from the harmful effects of a herbicide, which comprises applying to the locus of the useful plants the polymorphs of the invention.

In a still further aspect, the present invention provides a method for combating weeds in crops of useful plants, which comprises treating the useful plants, seeds or cuttings thereof or the locus of the useful plants simultaneously or at separate times with a herbicide and the polymorphs of the invention.

Any method of application to weeds/crop of useful plant, or locus thereof, which is routinely used in agriculture may be used, for example application by spray or broadcast method typically after suitable dilution of the composition of the invention.

The term "plant" as used herein includes seedlings, bushes and trees.

The term "locus" as used herein includes not only areas where weeds may already be growing, but also areas where weeds have yet to emerge, and also to areas under cultivation with respect to crops of useful plants. Areas under cultivation include land on which the crop plants are already growing and land intended for cultivation with such crop plants.

Crops of useful plants in which compositions of the invention may be used or the methods of the invention applied include perennial crops, such as citrus fruit, grapevines, nuts, oil palms, olives, pome fruit, stone fruit and rubber, and annual arable crops, such as cereals, for example barley and wheat, cotton, oilseed rape, maize (including sweet corn), rice, sorghum, soy beans, sugar beet, sugar cane, sunflowers, ornamentals and vegetables, especially cereals and maize.

Compositions and methods of the invention may also be used on turf, pasture, rangeland, rights of way etc. In particular they may be used on golf-courses, lawns, parks, sports-fields, race-courses and the like.

Plants are to be understood as also including those which have been rendered tolerant to herbicides or classes of herbicides (e.g. ALS-, GS-, EPSPS-, PPO- and HPPD-inhibitors) by conventional methods of breeding or by genetic engineering. An example of a plant that has been rendered tolerant to imidazolinones, e.g. imazamox, by conventional methods of breeding is Clearfield® summer rape (canola). Examples of plants that have been rendered tolerant to herbicides by genetic engineering methods include e.g. glyphosate- and glufosinate-resistant maize varieties commercially available under the trade names RoundupReady® and LibertyLink®.

Plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate. Traits include those that increase plant defences against insects, arachnids, nematodes and slugs and snails by virtue of toxins formed in the plants, in particular those formed in the plants by the genetic material from Bacillus thuringiensis (for example by the genes Cry1A(A1), Cry1A(b), Cry1A(c), Cry11A, Cry111A, CryIIIB2, Cry9c, Cry2Ab, Cry3Bb and Cry1F and also combinations thereof). Traits also include those that plant defences against fungi, bacteria and viruses by systemic acquired resistance (SAR), systemin, phytoalexins, elicitors and resistance genes and correspondingly expressed proteins and toxins.

Plants or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Plants are also to be understood as being those which are obtained by conventional methods of breeding or genetic engineering and contain so-called output traits (e.g. improved storage stability, higher nutritional value and improved flavor).

Plants and plant cultivars obtained by genetic engineering methods, if appropriate in combination with conventional methods, and parts thereof, may be treated by the polymorphs and compositions of the invention. Plant cultivars are understood as meaning plants having novel properties ("traits") which have been obtained by conventional breeding, by mutagenesis or by recombinant DNA techniques. These can be cultivars, bio- or genotypes. Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected. The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape.

The term "weeds" as used herein means any undesired plant, and thus includes not only agronomically important weeds as described below, but also volunteer crop plants.

The compositions according to the invention are suitable for all the conventional methods of application in agriculture, such as, e.g., pre-emergent application, post-emergent application and seed dressing. Depending on the intended use, a polymorph of the invention can be employed for pre-treatment of the seed of the crop plant (dressing of the seed or cuttings) or can be introduced into the soil before or after sowing. However, it can also be applied by itself or together with a herbicide before or after emergence of the plants. The treatment of the plants or seed with the polymorph can therefore in principle be carried out independently of the time of application of a herbicide. Treatment of the plants by simultaneous application of the herbicide and a polymorph (e.g. as a tank mix) is as a rule preferred. The application rate of polymorph to herbicide to be applied largely depends of the method of use. For field treatment, as a rule 0.001 to 5.0 kg of polymorph/ha, preferably 0.01 to 0.5 kg polymorph/ha and as a rule between 0.005 to 2 kg of herbicide/ha, but preferably between 0.001 to 1 kg/ha are applied. For seed dressing, in general 0.001 to 10 g of polymorph/kg seed, preferably 0.05 to 2 g polymorph/kg seed are applied.

The compositions of the invention (containing the polymorphs of the invention and preferably a herbicide) are preferably formulated in various ways using formulation components, such as carriers, solvents and surface-active substances, for example, as described hereinafter.

The formulated compositions can be in various physical forms. For compositions containing the polymorphs of the invention but no herbicidal active ingredient, these can be e.g. in the form of dusting powders, gels, wettable powders, water-dispersible granules, water-dispersible tablets, effervescent pellets, aqueous dispersions, oily dispersions, suspoemulsions, capsule suspensions, suspension concentrates, emulsifiable granules, impregnated polymer films or in other forms known e.g. from the Manual on Development and Use of FAO Specifications for Plant Protection Products, 5th Edition, 1999. Where one or more herbicides are combined with the polymorph of the invention, these may be present in a liquid or solid state: naming convention means that such formulations will be named according to the presentation of the herbicidal active ingredient and not the polymorph of the safener of compound I and so further formulation types are also possible. The formulated compositions can be in the form of concentrates which are diluted prior to use, although ready-to-use formulations can also be made. The dilutions can be made, for example, with water, liquid fertilisers, micronutrients, biological organisms, oil or solvents.

The formulated compositions can be prepared e.g. by mixing the polymorph and optional herbicide, with the formulation components in order to obtain compositions in the form of finely divided solids, granules or dispersions. The active ingredients can also be formulated with other components, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules usually have a diameter of from 0.1 to 500 microns. Typically, they will contain active ingredients in an amount of about from 25 to 95% by weight of the capsule weight. The active ingredients can be in the form of a monolithic solid or in the form of fine particles in solid or liquid dispersion. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other known polymers. Alternatively, very fine microcapsules can be formed in which the active ingredient is contained in the form of finely divided particles in a solid matrix of base substance, but the microcapsules are not themselves encapsulated.

The formulation components that are suitable for the preparation of compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid (e.g. butyl acetate, ethyl acetate, isoamyl acetate, amyl acetate), diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, methanol, ethanol, isopropanol, and alcohols of higher molecular weight, such as amyl alcohol, tetrahydrofurfuryl alcohol, hexanol, octanol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances may advantageously be used in the formulations, especially in those formulations designed to be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further components that can usually be used in such formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers. An example of such an adjuvant is ammonium sulphate.

The formulated compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_{8-22}$ fatty acids, especially the methyl derivatives of $C_{12-18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Another preferred adjuvant is Adigor® (Syngenta AG) which is a methylated rapeseed oil-based adjuvant.

The application and action of the oil additives can be further improved by combination with surface-active substances, such as non-ionic, anionic or cationic surfactants. Examples of suitable anionic, non-ionic and cationic surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12-22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

Formulated compositions of the invention generally comprise from 0.1 to 99% by weight, especially from 0.1 to 95% by weight, of the polymorph and a herbicide and from 1 to 99.9% by weight of a formulation adjuvant which preferably includes from 0 to 25% by weight of a surface-active substance. Whereas commercial products will preferably be formulated as concentrates, the end user will normally employ dilute formulations.

Various methods and techniques are suitable for using the polymorphs or compositions containing them for protecting crop plants from the harmful actions of herbicides, such as, for example, the following:

i) Seed dressing

Dressing of the seed with the polymorph formulated as a wettable powder by shaking in a vessel until uniform distribution over the seed surface is achieved (dry dressing). About 1 to 500 g of polymorph (4 g to 2 kg of wettable powder) per 100 kg of seed are used here.

The dressing of the seed or the treatment of the sprouted seed are of course the preferred methods of application, because the treatment with the polymorph is directed entirely at the target crop. As a rule, 1 to 1000 g of polymorph, preferably 5 to 250 g of polymorph are used per 100 kg of seed, it being possible to deviate upwards or downwards from the limit concentrations stated (repeat dressing), depending on the methods, which also allows the addition of other active compounds or micronutrients.

ii) Application as a tank mix

A liquid processed mixture of polymorph and herbicide (reciprocal ratio of amounts between 10:1 and 1:100) is used, the application rate of herbicide being 0.005 to 5.0 kg per hectare. Such tank mixes are applied before or after sowing.

iii) Application into the seed furrow

The polymorph is introduced into the open sown seed furrow as a wettable powder or as granules. After the seed furrow has been covered, the herbicide is applied by the pre-emergent method in a conventional method.

iv) Controlled release of the polymorph

The polymorph is absorbed in solution on to mineral carrier granules or polymerised granules (urea/formaldehyde) and dried. A coating which allows the polymorph to be released over a certain period of time can optionally be applied (coated granules).

In particular, preferred formulations have the following composition (%=percent by weight; active mixture of active compounds means the mixture of a compound of formula I with a herbicide):

Dusts

Active mixture of active compounds: 0.1 to 10%, preferably 0.1 to 5%

Solid carrier: 99.9% to 90%, preferably 99.9 to 99%

Suspension Concentrates

Active mixture of active compounds: 5 to 75%, preferably 10 to 50%

Water: 94 to 24%, preferably 88 to 30%

Surface-active agent: 1 to 40%, preferably 2 to 30%

Wettable Powders

Active mixture of active compounds: 0.5 to 90%, preferably 1 to 80%

Surface-active agent: 0.5 to 20%, preferably 10 to 15%

Solid carrier: 5 to 95%, preferably 15 to 90%

Granules

Active mixture of active compounds: 0.1 to 30%, preferably 0.1 to 15%

Solid carrier: 99.5 to 70%, preferably 97 to 85%

Formulation Examples for Mixtures of the Polymorph of the Invention with a Herbicides (%=% by Weight; EO=Ethylene Oxide)

Formulation 1. Wettable Powders

|  | a) | b) | c) | d) |
|---|---|---|---|---|
| active compound mixture | 5% | 25% | 50% | 80% |
| sodium lignosulfonate | 4% | — | 3% | — |
| sodium lauryl sulphate | 2% | 3% | — | 4% |
| sodium diisobutylnaphthalene-sulfonate | — | 6% | 5% | 6% |
| octylphenol polyglycol ether (7-8 mol EO) | — | 1% | 2% | — |
| highly dispersed silicic acid | 1% | 3% | 5% | 10% |
| kaolin | 88% | 62% | 35% | — |

The active compound mixture is mixed thoroughly with the adjuvants and the resulting mixture is thoroughly ground in a suitable mill, affording wettable powders which can be diluted with water to give suspensions of any desired concentration.

Formulation 2. Coated Granules

|  | a) | b) | c) |
|---|---|---|---|
| active compound mixture | 0.1% | 5% | 15% |
| highly dispersed silicic acid | 0.9% | 2% | 2% |
| inorganic carrier (diameter 0.1-1 mm) e.g. CaCO$_3$ or SiO$_2$ | 99.0% | 93% | 83% |

The active compound mixture is dissolved in methylene chloride and applied to the carrier by spraying, and the solvent is then evaporated off in vacuo.

Formulation 3. Coated Granules

|  | a) | b) | c) |
|---|---|---|---|
| active compound mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. CaCO$_3$ or SiO$_2$ | 98.0% | 92% | 80% |

The finely ground active compound mixture is uniformly applied, in a mixer, to the carrier moistened with polyethylene glycol. Non-dusty coated granules are obtained in this manner.

Formulation 4. Extruded Granules

|  | a) | b) | c) | d) |
|---|---|---|---|---|
| active compound mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active compound mixture is mixed and ground with the adjuvants, and the mixture is moistened with water. The mixture is extruded and then dried in a stream of air.

Formulation 5. Dusts

|  | a) | b) | c) |
|---|---|---|---|
| active compound mixture | 0.1% | 1% | 5% |
| talcum | 39.9% | 49% | 35% |
| kaolin | 60.0% | 50% | 60% |

Ready-to-use dusts are obtained by mixing the active compound mixture with the carriers and grinding the mixture in a suitable mill.

Formulation 6. Suspension Concentrates

|  | a) | b) | c) | d) |
|---|---|---|---|---|
| active compound mixture | 3% | 10% | 25% | 50% |
| ethylene glycol | 5% | 5% | 5% | 5% |
| nonylphenol polyglycol ether (15 mol EO) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active compound mixture is intimately mixed with the adjuvants, giving a suspension concentrate from which suspensions of any desired concentration can be obtained by dilution with water.

It is often more practical to formulate the polymorph and the herbicide individually and then to bring them together as a 'tank mix' in water in the application equipment in the desired mixing ratio shortly before application.

The compositions and formulations of the present invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth form yet further aspects of the invention.

Where a polymorph of the invention, in particular, the Form 2 polymorph, is combined with at least one herbicide, the following herbicides are particularly preferred: acetochlor, acifluorfen, acifluorfen-sodium, aclonifen, acrolein, alachlor, alloxydim, allyl alcohol, ametryn, amicarbazone, amidosulfuron, aminocyclopyrachlor, aminopyralid, amitrole, ammonium sulfamate, anilofos, asulam, atrazine, aviglycine, azafenidin, azimsulfuron, BCPC, beflubutamid, benazolin, bencarbazone, benfluralin, benfuresate, bensulfuron, bensulfuron-methyl, bensulide, bentazone, benzfendizone, benzobicyclon, benzofenap, bicyclopyrone, bifenox, bilanafos, bispyribac, bispyribac-sodium, borax, bromacil, bromobutide, bromophenoxim, bromoxynil, butachlor, butafenacil, butamifos, butralin, butroxydim, butylate, cacodylic acid, calcium chlorate, cafenstrole, carbetamide, carfentrazone, carfentrazone-ethyl, CDEA, CEPC, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, CMA, 4-CPB, CPMF, 4-CPP, CPPC, cresol, cumyluron, cyanamide, cyanazine, cycloate, cyclosulfamuron, cycloxydim, cyhalofop, cyhalofop-butyl, 2,4-D, 3,4-DA, daimuron, dalapon, dazomet, 2,4-DB, 3,4-DB, 2,4-DEB, desmedipham, desmetryn, dicamba, dichlobenil, ortho-dichlorobenzene, para-dichlorobenzene, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, dipropetryn, diquat, diquat dibromide, dithiopyr, diuron, DNOC, 3,4-DP, DSMA, EBEP, endothal, EPTC, esprocarb, ethalfluralin, ethametsulfuron, ethametsulfuron-methyl, ethephon, ethofumesate, ethoxyfen, ethoxysulfuron, etobenzanid, fenoxaprop, fenoxaprop-P, fenoxaprop-ethyl, fenoxaprop-P-ethyl, fenoxasulfone, fentrazamide, ferrous sulfate, flamprop-M, flazasulfuron, florasulam, fluazifop, fluazifop-butyl, fluazifop-P, fluazifop-P-butyl, fluazolate, flucarbazone, flucarbazone-sodium, flucetosulfuron, fluchloralin, flufenacet, flufenpyr, flufenpyr-ethyl, flumetralin, flumetsulam, flumiclorac, flumiclorac-pentyl, flumioxazin, flumipropin, fluometuron, fluoroglycofen, fluoroglycofen-ethyl, fluoxaprop, flupoxam, flupropacil, flupropanate, flupyrsulfuron, flupyrsulfuron-methyl-sodium, flurenol, fluridone, fluorochloridone, fluoroxypyr, flurtamone, fluthiacet, fluthiacet-methyl, fomesafen, foramsulfuron, fosamine, glufosinate, glufosinate-ammonium, glyphosate, halosulfuron, halosulfuron-methyl, haloxyfop, haloxyfop-P, HC-252, hexazinone, imazamethabenz, imazamethabenz-methyl, imazamox, imazapic, imazapyr, imazaquin, imazethapyr, imazosulfuron, indanofan, indaziflam, iodomethane, iodosulfuron, iodosulfuron-methyl-sodium, ioxynil, ipfencarbazone, isoproturon, isouron, isoxaben, isoxachlortole, isoxaflutole, isoxapyrifop, karbutilate, lactofen, lenacil, linuron, MAA, MAMA, MCPA, MCPA-thioethyl, MCPB, mecoprop, mecoprop-P, mefenacet, mefluidide, mesosulfuron, mesosulfuron-methyl, mesotrione, metam, metamifop, metamitron, metazachlor, metazosulfuron, methabenzthiazuron, methazole, methylarsonic acid, methyldymron, methyl isothiocyanate, metobenzuron, metobromuron, metolachlor, S-metolachlor, metosulam, metoxuron, metribuzin, metsulfuron, metsulfuron-methyl, MK-616, molinate, monolinuron, monosulfuron, monosulfuron-ester, MSMA, naproanilide, napropamide, naptalam, NDA-402989, neburon, nicosulfuron, nipyraclofen, n-methyl glyphosate, nonanoic acid, norflurazon, oleic acid (fatty acids), orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, petrolium oils, phenmedipham, phenmedipham-ethyl, picloram, picolinafen, pinoxaden, piperophos, potassium arsenite, potassium azide, pretilachlor, primisulfuron, primisulfuron-methyl, prodiamine, profluazol, profoxydim, prohexadione-calcium, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxulam, quinclorac, quinmerac, quinoclamine, quizalofop, quizalofop-P, quizalofop-ethyl, quizalofop-P-ethyl, rimsulfuron, saflufenacil, sethoxydim, siduron, simazine, simetryn, SMA, sodium arsenite, sodium azide, sodium chlorate, sulcotrione, sulfentrazone, sulfometuron, sulfometuron-methyl, sulfosate, sulfosulfuron, sulfuric acid, tar oils, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazafluoron, thiazopyr, thifensulfuron, thiencarbazone, thifensulfuron-methyl, thiobencarb, tiocarbazil, topramezone, tralkoxydim, triafamone, tri-allate, triasulfuron, triaziflam, tribenuron, tribenuron-methyl, tricamba, triclopyr, trietazine, trifloxysulfuron, trifloxysulfuron-sodium, trifluralin, triflusulfuron, triflusulfuron-methyl, trifop, trifop-methyl, trihydroxytriazine, trinexapac-ethyl, tritosulfuron, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), 4-amino-3-chloro-6-(4-chloro-2-fluoro-3-methoxyphenyl)-2-pyridinecarboxylic acid (CAS RN 943832-60-8) and 4-hydroxy-3-[[2-(3-methoxypropyl)-6-(difluoromethyl)-3-pyridinyl]carbonyl]-bicyclo[3.2.1]oct-3-en-2-one.

Particularly preferred combinations are the polymorph of Form 2 and ametryn, atrazine, bicyclopyrone, cinosulfuron, clodinafop-propargyl, clomazone, dicamba, dimethachlor, diquat, fluazifop-p-butyl, fomesafen, glyphosate, mesotrione, molinate, napropamide, S-metolachlor, nicosulfuron, paraquat, pinoxaden, pretilachlor, primisulfuron, prometryn, prosulfocarb, prosulfuron, pyridate, pyriftalid, tralkoxydim, triasulfuron and trifloxysulfuron-sodium.

Whilst compositions comprising the polymorph of the invention and another herbicide are explicitly disclosed above, the skilled man will appreciate that the invention extends to three-way, and further multiple combinations comprising the above two-way mixtures.

For the avoidance of doubt, even if not explicitly stated above, the mixing partners of may also be in the form of any suitable agrochemically acceptable ester or salt, as mentioned e.g. in The Pesticide Manual, Thirteenth Edition, British Crop Protection Council, 2003.

Various aspects and embodiments of the present invention will now be illustrated in more detail by way of example and the following Figure in which.

EXAMPLES

1. Preparation of Polymorphs

Figure 1:
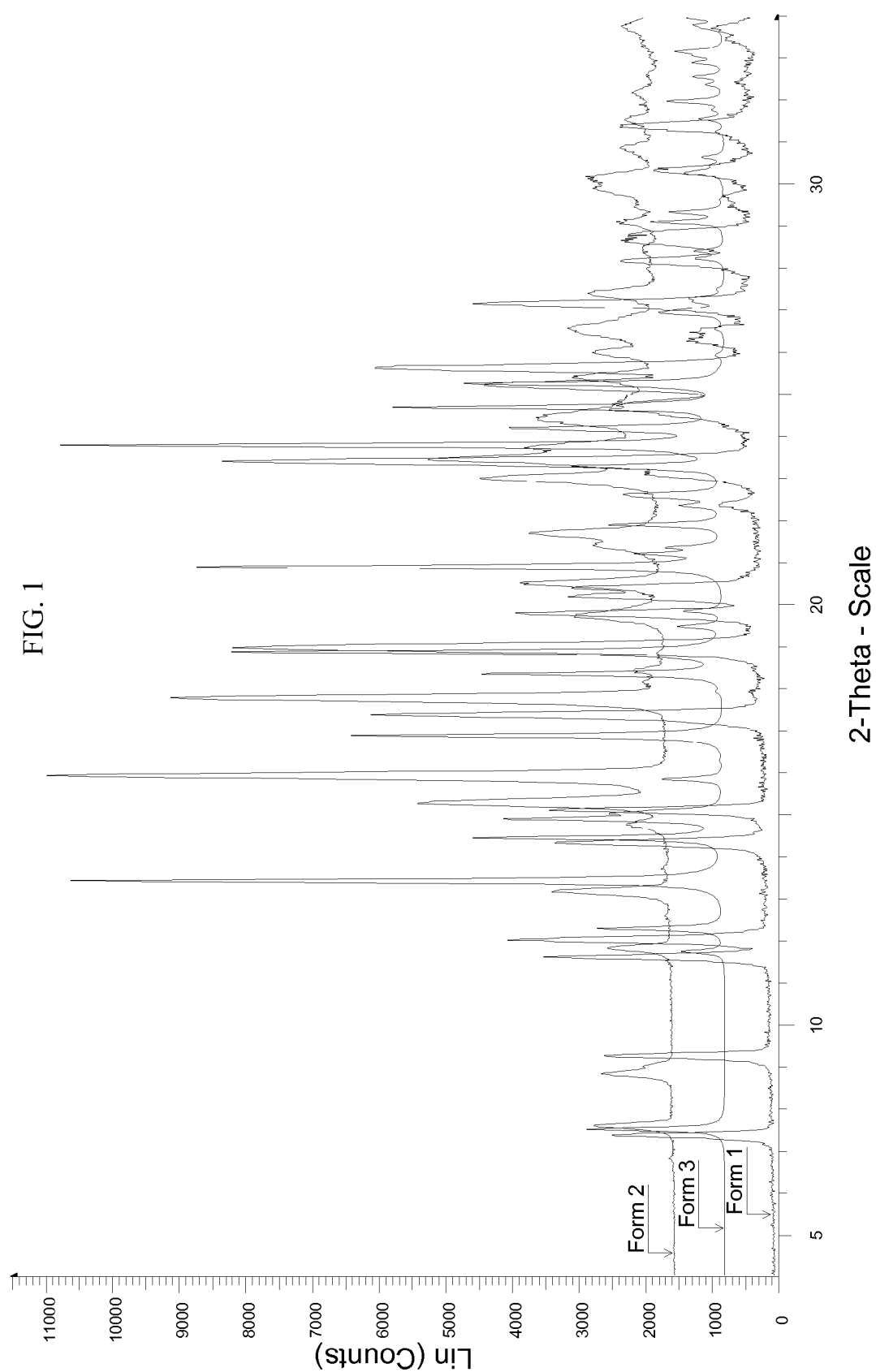
FIG. 1 shows the powder X-ray diffraction patterns of the polymorphs of N-(2-methoxybenzoyl)-4-[(methylaminocarbonyl)amino]benzenesulfonamide named as Form 1, Form 2 and Form 3, wherein the diffraction traces of Form 2 and 3 are those predicted from the single crystal structure and that of Form 1 is obtained through powder X-ray diffraction analysis.
Figure 2:
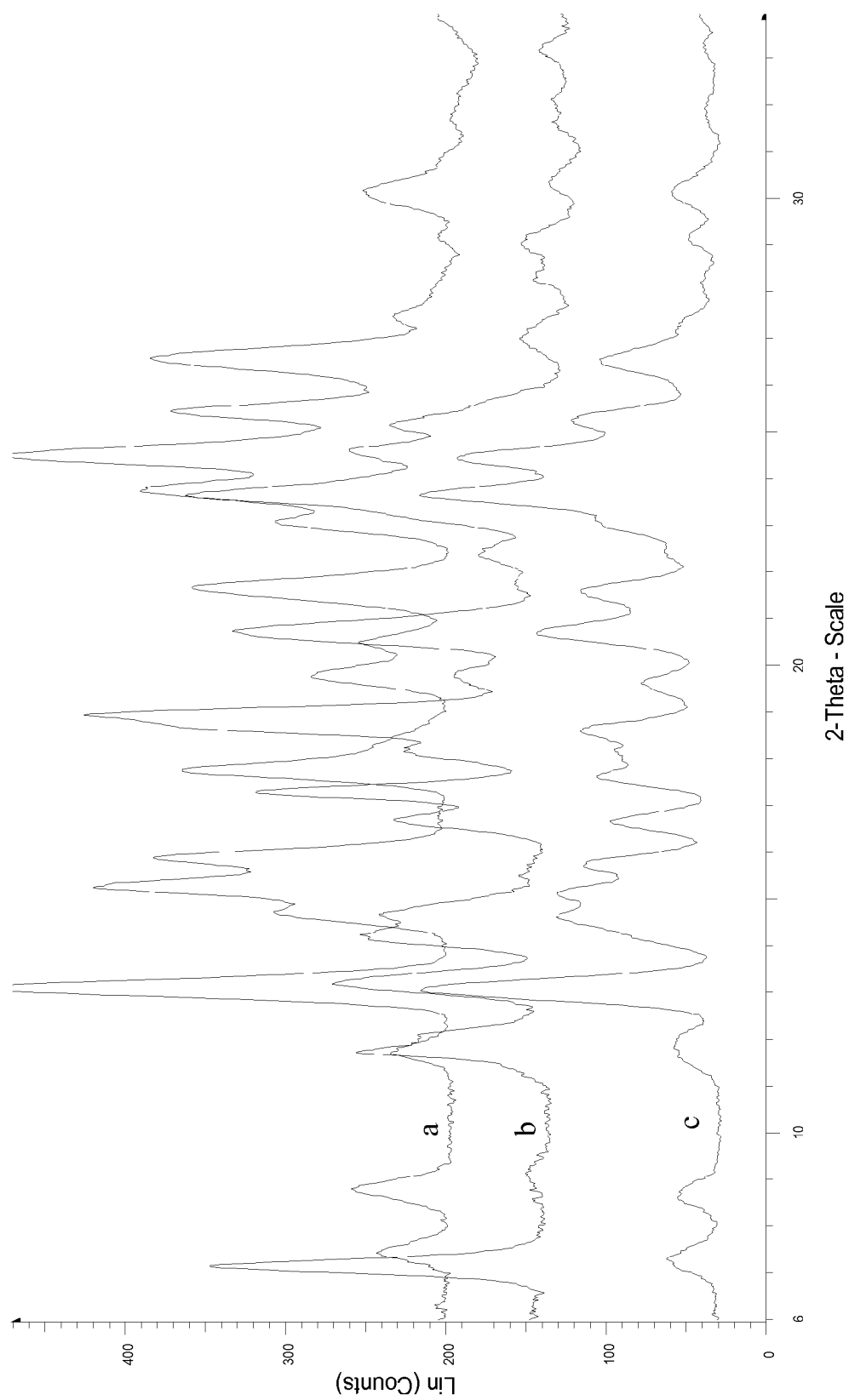
FIG. 2 shows the powder X-Ray diffraction patterns of (a) Form 2, (b) Form 3 and (c) 50° C. slurry analysed after 2 days.

The compound of formula (I) was prepared as described in U.S. Pat. No. 5,215,570.
1a Preparation of Polymorph Form 1
The compound of formula (I) prepared as described in U.S. Pat. No. 5,215,570, is taken up in ice water and the precipitated product is separated off and dried, yielding polymorph Form 1.
1b. Preparation of Polymorph Form 2
55 ml of acetone was added to 4.6 g of polymorph Form 1 and heated to reflux (56° C.). 3 mls of water was added to form a pale yellow solution which was allowed to cool slowly. The resultant crystals were isolated by filtration and dried. DSC analysis confirmed the presence of polymorph Form 2 with a melting point of 215° C.

1c. Seeded Slurry Conversion of Form 1 to Form 2
300 g of polymorph Form 1 was stirred with 1500 g 30% water/acetone and heated to 60° C. The slurry was seeded with 3 g of polymorph Form 2. The conversion of Form 1 to Form 2 was monitored by DSC—after 1 hour, Form 1 was not detected by DSC. The crystals were collected by filtration under reduced pressure at 60° C., sucked dry on the filter and then dried to constant weight in a vacuum oven at 40° C. The oven drying took 4 hours and 200 g polymorph Form 2 was produced with 97% purity (as assessed by DSC).
1d. Preparation of Crystals of Polymorph Form 2 for Single Crystal Analysis
0.5 g of polymorph Form 2 and 2 g of 50% ethyl acetate/acetonitrile were mixed. The resultant solution was left for 120 days. During this time, the solvent level dropped and crystals became visible. The lid was removed from the vial and the remaining solvent allowed to evaporate before the crystals were collected and analysed.
1e. Preparation of Polymorph Form 3
0.2 g of polymorph Form 1 was dissolved in 15 to 20 mls of acetone at 45° C. Water was added to give a water/acetone composition of 25% water. The resultant precipitate is stirred at 45° C. Samples taken after 30 minutes showed the presence of polymorph Form 1. Samples taken after 5, 7 and 20 days show the presence of polymorph Form 3.

2. Analysis of Polymorphs

After preparation by the methods detailed above, the samples were subject to analysis by powder X-ray diffraction and/or single crystal X-ray diffraction and/or differential scanning calorimetry (DSC).

Powder X-ray diffraction analysis of solid material was carried out using the Briker D8 powder diffractometer. Samples were mounted in Perspex sample holders and the samples flattened. The sample holder was rotated and X-rays were collected from 4° to 34° 2-theta, with a scan time of 25 to 30 minutes depending on the pattern intensity.

Single crystal intensity data was collected on an Oxford Xcalibar PX Ultra diffractometer using Cu Kα radiation (($\lambda$=1.54056 Å) with a graphite monochromator. The crystal was mounted in NVH oil at room temperature for data collection. The data was solved using the CRYSTALS software package.

DSC was carried out using a Mettler Toledo DSC 820 pr DSC1. A sample loading of around 5 mg was used and this was heated from 25° C. to 250° C. at a rate of 10° C./minute on the DSC820 or from 40° C. to 250° C. at a rate of 10° C./minute on the DSC1. The lid of the DSC crucible was pierced to allow the escape of any gas formed during the heating of the sample.

3. Stability of Polymorphs

Approximately 0.1 g each of Form 1, Form 2 and Form 3 were added to 10 ml of ethanol at 50° C. and 60° C. until there were solids out of solution (a slurry). The temperature was maintained with stirring and the crystal form examined after 2 and 8 days.

At 50° C. and 60° C. after 2 days, Form 2 and Form 3 were still present as seen in FIG. 1. There was no evidence of Form 1.

Figure 3:
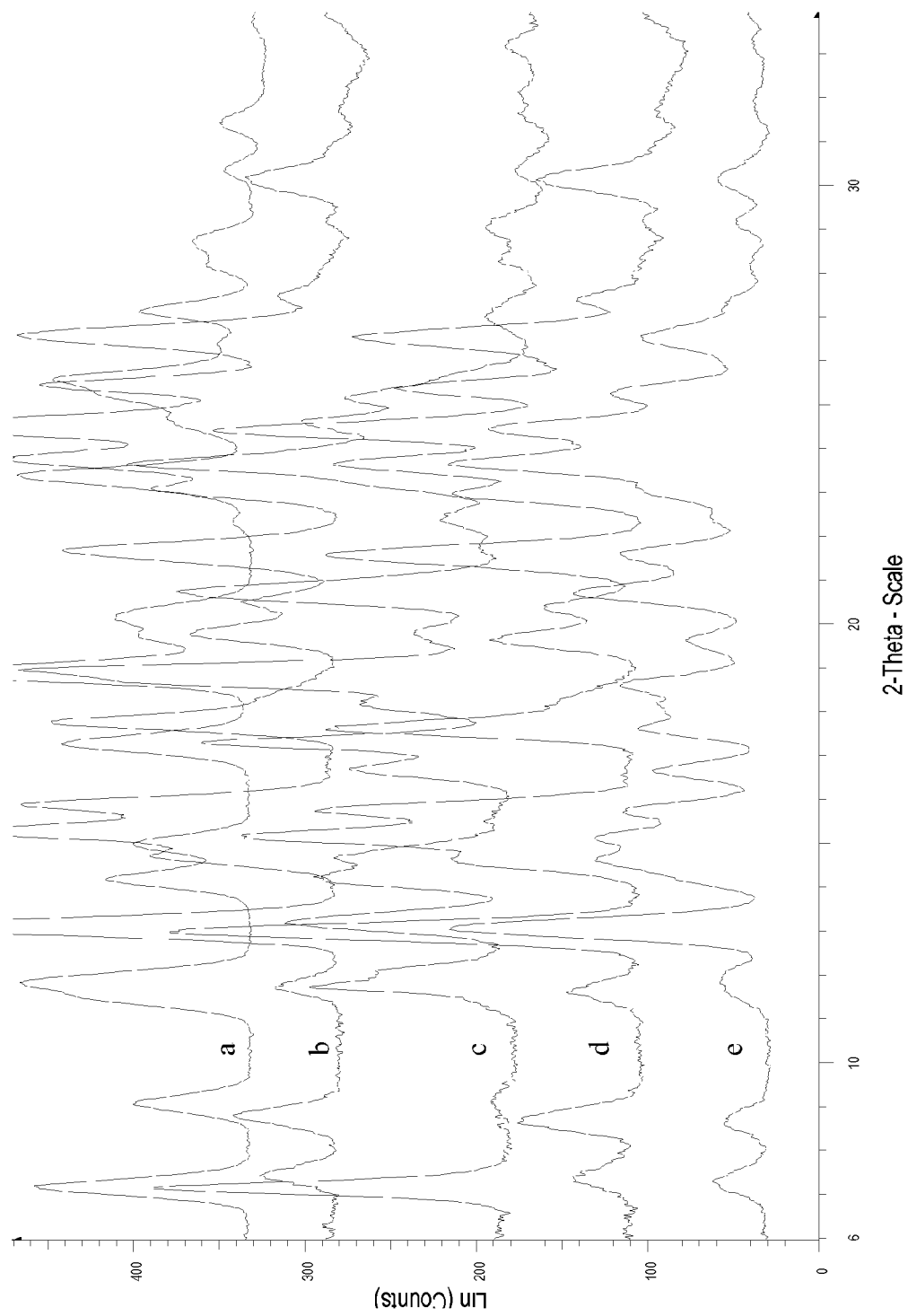
FIG. 3 shows the powder X-Ray diffraction patterns of (a) Form 1, (b) Form 2, (c) Form 3 and (d) 50° C. slurry analysed after 2 days (e) 60° C. slurry analysed after 2 days.
Figure 4:
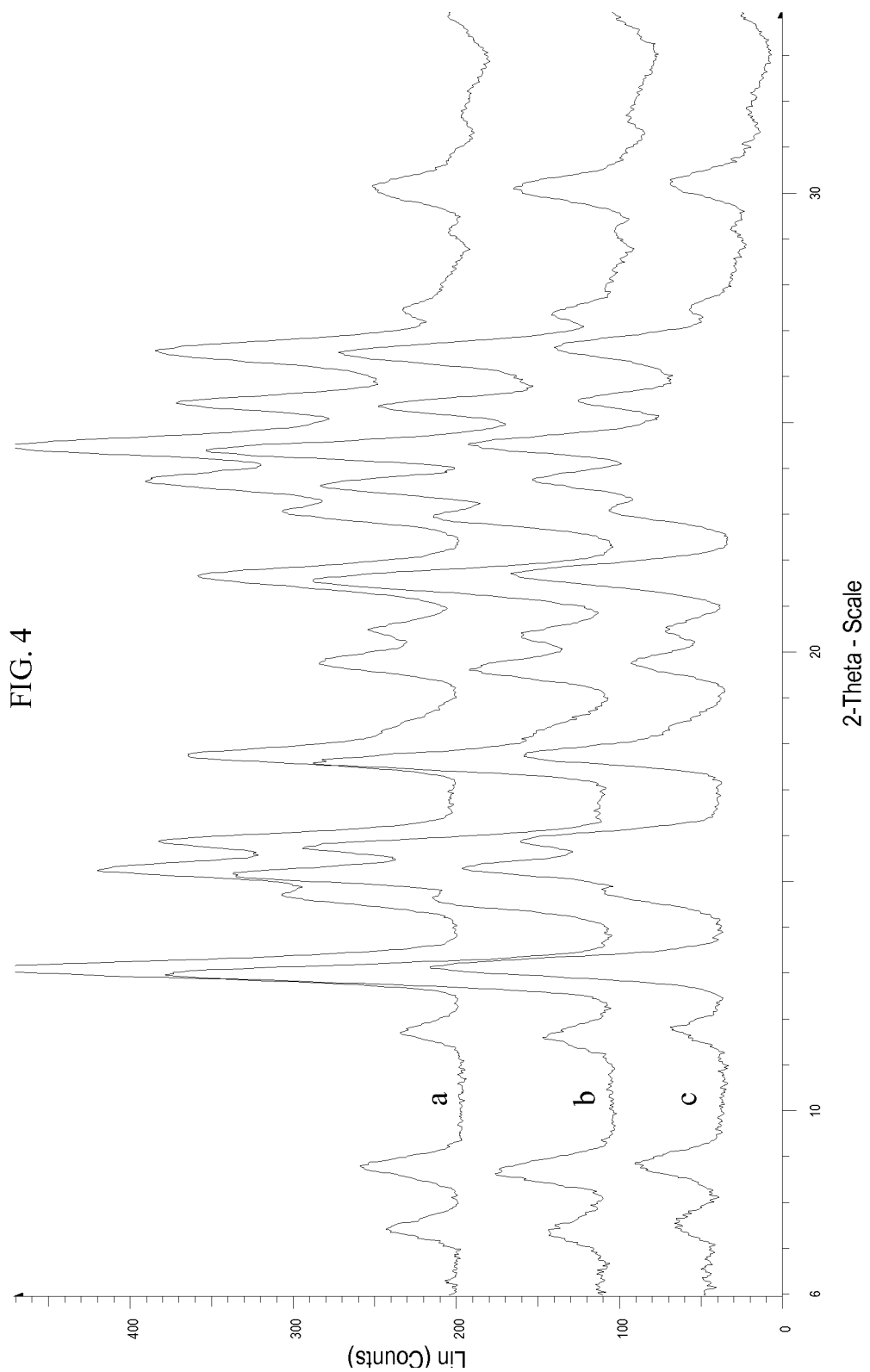
FIG. 4 shows the powder X-Ray diffraction patterns of (a) Form 2, (b) 60° C. slurry analysed after 8 days and (c) 50° C. slurry analysed after 8 days.
Figure 5:
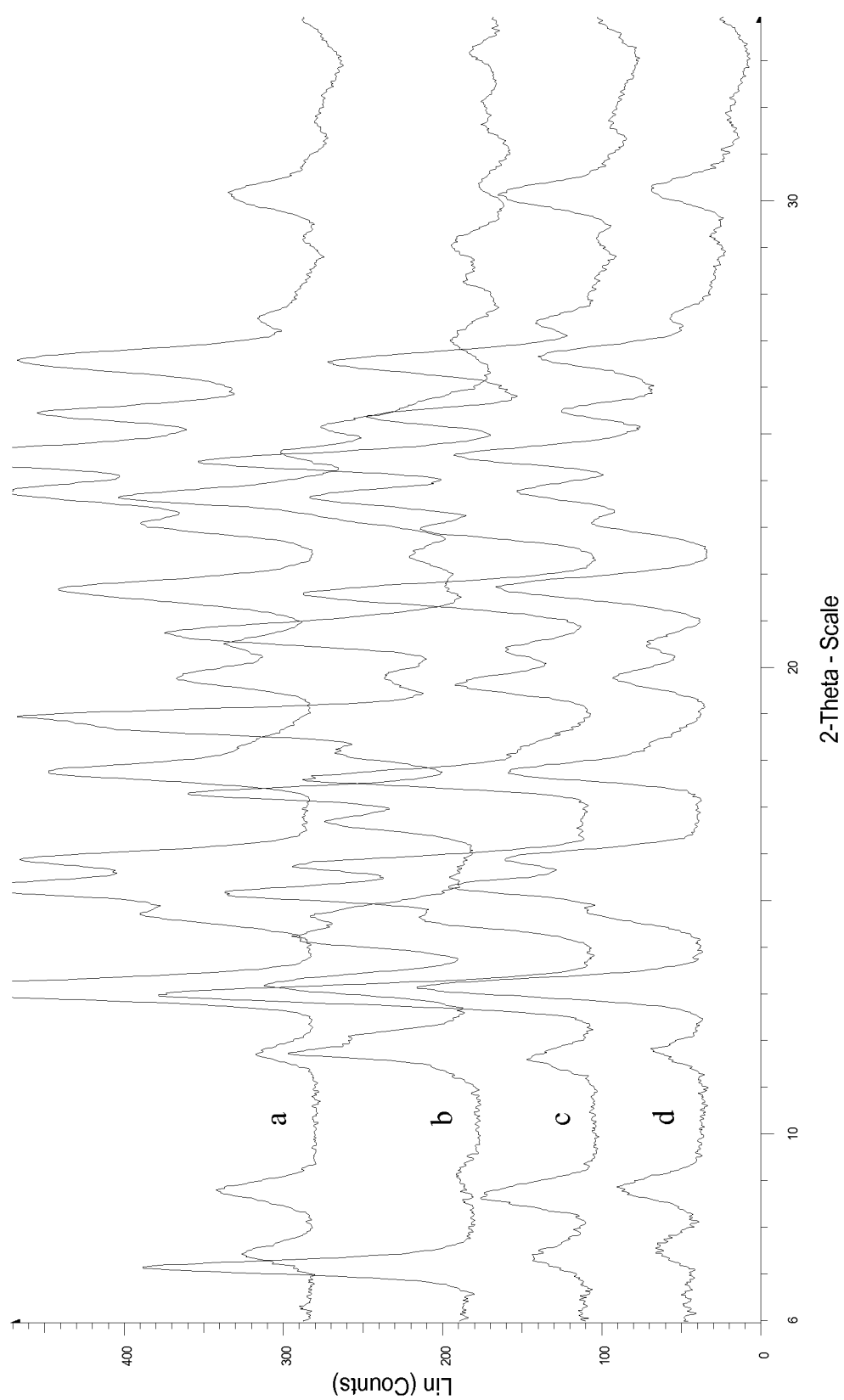
FIG. 5 shows the powder X-Ray diffraction patterns of (a) Form 2 (b) Form 3, (c) 60° C. slurry analysed after 8 days and (d) 50° C. slurry analysed after 8 days.

Further slurrying for 8 days in total showed complete conversion to Form 2 at both temperatures, see FIG. 3.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A crystalline polymorph of the compound of formula I:

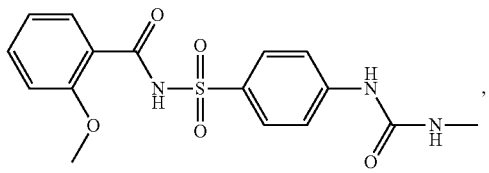
(I)

wherein the polymorph is characterised by a powder X-ray diffraction pattern expressed in terms of 2θ angles, wherein the powder X-ray diffraction pattern comprises:
(a) at least one 2θ angle value at 9.0±0.2; and
(b) one 2θ angle value at 21.7±0.2; and
(c) at least three 2θ angle values selected from the group comprising 7.7±0.2, 11.9±0.2, 13.4±0.2, 15.0±0.2, 15.6±0.2, 16.1±0.2 and 18.0±0.2.

2. The crystalline polymorph of claim 1 which has a melting point of 216° C.±5° C.

3. The crystalline polymorph of claim 1 which has the following lattice parameters: a=19.38(5), b=7.34(5), c=22.95(5), α=90.00, β=90.00, γ=90.00 and volume=3264.8(5) Å³.

4. An agricultural composition comprising a polymorph chosen from at least one of
a crystalline polymorph of the compound of formula I

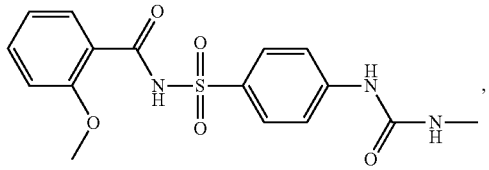
(I)

which has the following lattice parameters: a=19.38(5), b=7.34(5), c=22.95(5), α=90.00, β=90.00, γ=90.00 and volume=3264.8(5) Å³; and
a crystalline polymorph of the compound of formula I

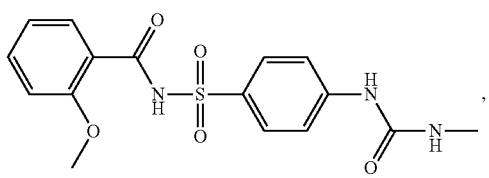
(I)

wherein the polymorph is characterised by a powder X-ray diffraction pattern expressed in terms of 2θ angles, wherein the powder X-ray diffraction pattern comprises:
(a) at least one 2θ angle value at 9.0±0.2; and
(b) one 2θ angle value at 21.7±0.2; and
(c) at least three 2θ angle values selected from the group comprising 7.7±0.2, 11.9±0.2, 13.4±0.2, 15.0±0.2, 15.6±0.2, 16.1±0.2 and 18.0±0.2; and at least one agriculturally acceptable carrier or diluent.

5. The composition of claim 4, which further comprises at least one herbicide.

6. A method for protecting crops of useful plants from the harmful effects of a herbicide, which comprises applying to the locus of the useful plants a composition of claim 4.

7. A method for combating weeds in crops of useful plants, which comprises treating the useful plants, seeds or cuttings thereof or the locus of the useful plants simultaneously or at separate times with a herbicide and a polymorph chosen from at least one of
a crystalline polymorph of the compound of formula I

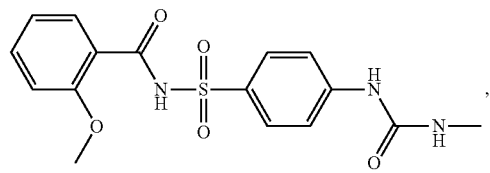
(I)

which has the following lattice parameters: a=19.38(5), b=7.34(5), c=22.95(5), α=90.00, β=90.00, γ=90.00 and volume=3264.8(5) Å³; and
a crystalline polymorph of the compound of formula I

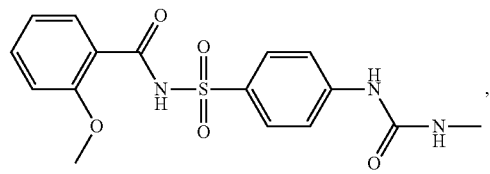
(I)

wherein the polymorph is characterised by a powder X-ray diffraction pattern expressed in terms of 2θ angles, wherein the powder X-ray diffraction pattern comprises:
(a) at least one 2θ angle value at 9.0±0.2; and
(b) one 2θ angle value at 21.7±0.2; and
(c) at least three 2θ angle values selected from the group comprising 7.7±0.2, 11.9±0.2, 13.4±0.2, 15.0±0.2, 15.6±0.2, 16.1±0.2 and 18.0±0.2.

* * * * *